United States Patent
Fukumoto et al.

(10) Patent No.: US 8,603,548 B2
(45) Date of Patent: Dec. 10, 2013

(54) ANTI-AVIAN INFLUENZA VIRUS AGENT, AND PRODUCT CONTAINING ANTI-AVIAN INFLUENZA VIRUS AGENT

(75) Inventors: Syuichi Fukumoto, Kitanagoya (JP); Kenji Kumagai, Kitanagoya (JP); Yasuo Suzuki, Kasugai (JP); Nongluk Sriwilaijaroen, Kasugai (JP)

(73) Assignee: Pokka Corporation, Aichi (JP)

( * ) Notice: Subject to any disclaimer, the term of this patent is extended or adjusted under 35 U.S.C. 154(b) by 232 days.

(21) Appl. No.: 13/122,709

(22) PCT Filed: Oct. 8, 2009

(86) PCT No.: PCT/JP2009/067533
§ 371 (c)(1),
(2), (4) Date: Apr. 5, 2011

(87) PCT Pub. No.: WO2010/041702
PCT Pub. Date: Apr. 15, 2010

(65) Prior Publication Data
US 2011/0195135 A1 Aug. 11, 2011

(30) Foreign Application Priority Data
Oct. 8, 2008 (JP) ................................. 2008-262199

(51) Int. Cl.
*A61K 36/00* (2006.01)
(52) U.S. Cl.
USPC .......................................... 424/725; 424/774
(58) Field of Classification Search
None
See application file for complete search history.

(56) References Cited

U.S. PATENT DOCUMENTS

| 6,841,174 | B2 * | 1/2005 | Shalaby et al. ................ 424/725 |
| 2003/0113388 | A1 * | 6/2003 | Phan ............................. 424/756 |
| 2003/0130208 | A1 * | 7/2003 | Obendorf et al. ................ 514/27 |
| 2003/0161903 | A1 * | 8/2003 | Konishi et al. ................. 424/776 |
| 2008/0293644 | A1 * | 11/2008 | Eidenberger .................... 514/25 |
| 2009/0196872 | A1 | 8/2009 | Kato et al. |
| 2010/0233256 | A1 * | 9/2010 | Zelkha et al. ................. 424/456 |

FOREIGN PATENT DOCUMENTS

| JP | 08099893 | A | * | 4/1996 |
| JP | 2000-273048 | A | | 10/2000 |
| JP | 2004250406 | A | * | 9/2004 |
| JP | 2006-055038 | A | | 3/2006 |
| JP | 2006056793 | A | * | 3/2006 |
| JP | 2006-199631 | A | | 8/2006 |
| JP | 2006273843 | A | * | 10/2006 |
| JP | 2008-088116 | A | | 4/2008 |
| JP | 2008-515906 | A | | 5/2008 |
| JP | 2008-522610 | A | | 7/2008 |
| WO | 2006/041978 | A2 | | 4/2006 |
| WO | 2006/061723 | A2 | | 6/2006 |
| WO | 2006090206 | A1 | | 8/2006 |
| WO | 2007/135774 | A1 | | 11/2007 |

OTHER PUBLICATIONS

"International Preliminary Report on Patentability for International Application No. PCT/JP2009/067533 with a Filing Date of Oct. 8, 2009," Patent Cooperation Treaty, Report completed by Authorized Officer, Gijsbertus Beijer on Jun. 7, 2011. 6 pages.
Deguchi et al., "Anti-Viral Agent Comprising Guava Leaf Extract as the Active Ingredient", World Patent Index Database Search Report, (Sep. 24, 2012).
Alexander, Dennis J., "A Review of Avian Influenza in Different Bird Species." Veterinary Microbiology, vol. 74, No. 1-2, p. 3-13, (May 1, 2000).
Arima et al., "Isolation of Antimicrobial Compounds from Guava (*Psidium guajava* L.) and their Structural Elucidation." Biosci. Biotechnol. Biochem. 66; 8 (2002): 1727-1730.
Mercadante et al., "Carotenoids from Guava (*Psidium guajava* L.): Isolation and Structure Elucidation." J. Agric. Food Chem., vol. 47, No. 1, (Jan. 1, 1999): p. 145-151.
Supplementary European Search Report, Sep. 28, 2012.

* cited by examiner

*Primary Examiner* — Chris R Tate
(74) *Attorney, Agent, or Firm* — Seager, Tufte & Wickhem LLC

(57) ABSTRACT

An anti-avian influenza virus agent containing, as an active ingredient, a component obtained when a guava extract extracted from a guava with an extraction solvent consisting primarily of at least one of water and a hydrophilic organic solvent is subjected to fractionation by HPLC under specific conditions. The specific conditions include the use of an ODS column, the use of a water-methanol mixture having a methanol concentration of 20% as a mobile phase during a period until 15 minutes after applying the guava extract to the column, and the use of a water-methanol mixture having a methanol concentration of 40% as a mobile phase during a subsequent period of 15 to 30 minutes. Alternatively, the specific conditions further include the use of a water-methanol mixture having a methanol concentration of 60% as a mobile phase during a period of 30 to 45 minutes after applying the guava extract to the column. The component contained in the anti-avian influenza virus agent is eluted from the column in a period until 20 minutes after applying the guava extract to the column or in a subsequent period of 20 to 35 minutes.

12 Claims, 4 Drawing Sheets

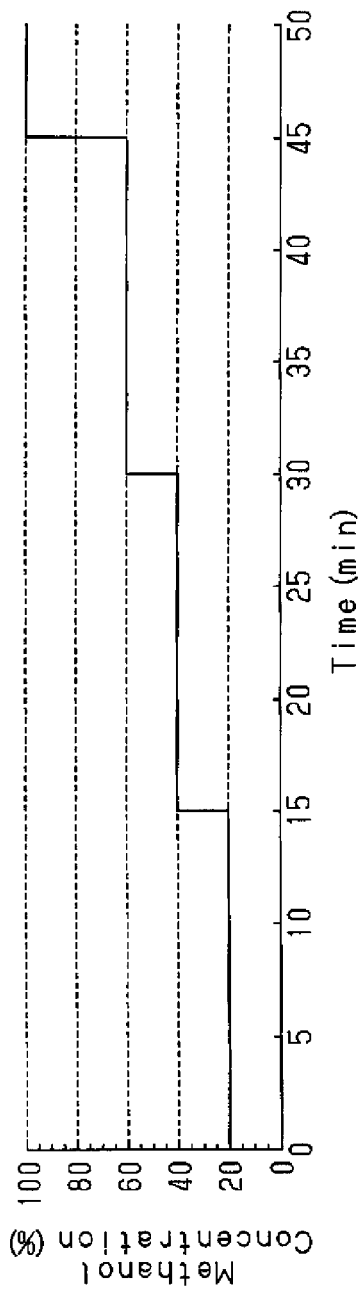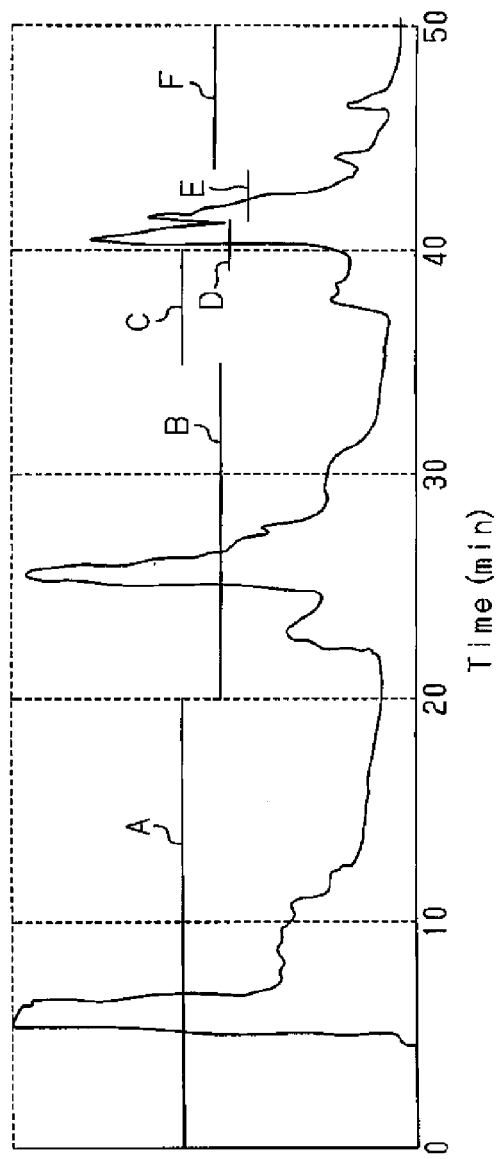
Fig.1(a)
Fig.1(b)

ANTI-AVIAN INFLUENZA VIRUS AGENT, AND PRODUCT CONTAINING ANTI-AVIAN INFLUENZA VIRUS AGENT

TECHNICAL FIELD

The present invention relates to an anti-avian influenza virus agent and a product containing the anti-avian influenza virus agent.

BACKGROUND ART

Avian influenza virus is a generic name for influenza A viruses that mainly infect birds, and wild water birds are their natural hosts. Some avian influenza viruses infect domestic poultry, such as chickens, quails, and turkeys, leading to highly pathogenic infection. The chicken industry is facing a worldwide threat from such highly pathogenic avian influenza viruses.

Although development and research of vaccines for preventing avian influenza virus infection have been conducted (see for example, Patent Document 1), no vaccine is currently available that can completely prevent avian influenza virus infection. The actual measure taken when an avian influenza virus infection actually breaks out is therefore to immediately destroy domestic poultry within a several-kilometer radius from the breakout site. The infection of H5N1 subtype virus, a subtype of avian influenza virus, has also been reported to occur in humans upon contact with a large amount of the virus or due to constitutional predisposition of a host.

PRIOR ART DOCUMENT

Patent Document 1: Japanese National Phase Laid-Open Patent Publication No. 2008-515906

SUMMARY OF INVENTION

Problems that the Invention is to Solve

The inventors of the present invention conducted various research studies and found, as a result, that a component derived from a guava extract has an anti-avian influenza virus effect. The present invention was achieved based on this finding. An objective of the present invention is to provide an anti-avian influenza virus agent and an anti-avian influenza virus agent-containing product with an excellent anti-avian influenza virus effect.

Means for Solving the Problems

To achieve the foregoing objective, one aspect of the present invention provides an anti-avian influenza virus agent containing, as an active ingredient, a component that is obtained when a guava extract extracted from a guava with an extraction solvent consisting primarily of at least one of water and a hydrophilic organic solvent is subjected to fractionation by high performance liquid chromatography (HPLC) under specific conditions. The specific conditions include the use of an ODS column having an inside diameter of 20 mm and a length of 250 mm, the use of a water-methanol mixture having a methanol concentration of 20% as a mobile phase during a period until 15 minutes after applying the guava extract to the ODS column, the use of a water-methanol mixture having a methanol concentration of 40% as a mobile phase during a subsequent period of 15 to 30 minutes, and the mobile phases being flowed at a rate of 10 mL/min. The component contained in the anti-avian influenza virus agent is eluted from the ODS column in a period until 20 minutes after applying the guava extract to the column.

Another aspect of the present invention provides an anti-avian influenza virus agent containing, as an active ingredient, a component eluted from the ODS column in a period of 20 to 35 minutes after applying the guava extract to the column, wherein the specific conditions further include the use of a water-methanol mixture having a methanol concentration of 60% as a mobile phase during a period of 30 to 45 minutes after applying the guava extract to the ODS column.

Another aspect of the present invention provides an anti-avian influenza virus agent-containing product containing one of the above-mentioned anti-avian influenza virus agents.

EFFECTS OF THE INVENTION

The present invention provides an anti-avian influenza virus agent and an anti-avian influenza virus agent-containing product with an excellent anti-avian influenza virus effect.

BRIEF DESCRIPTION OF DRAWINGS

FIG. 1(a) is a graph showing a gradient curve of the mobile phase used for the fractionation of a guava extract by high performance liquid chromatography;

FIG. 1(b) is an HPLC chart obtained from the fractionation of a guava extract by high performance liquid chromatography;

MODE FOR CARRYING OUT THE INVENTION

Figure 2A:
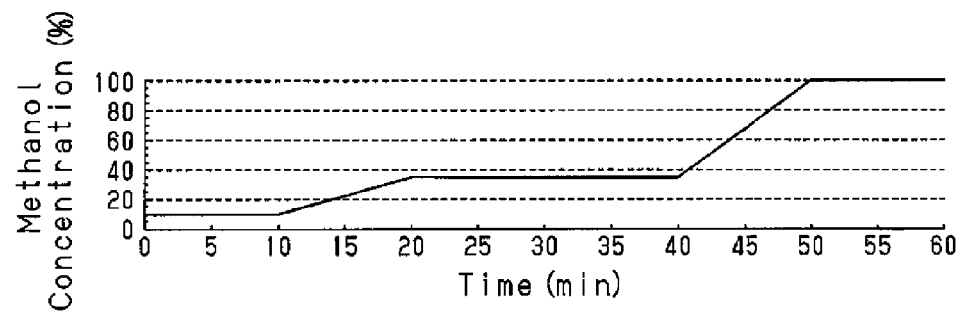
FIG. 2(a) is a graph showing a gradient curve of the mobile phase used for high performance liquid chromatography analysis of samples A to F and sample Mx.

Hereafter, one embodiment of the present invention will be described in detail.

An anti-avian influenza virus agent according to this embodiment contains, as an active ingredient, a component obtained in a specific elution time when a guava extract extracted from a guava (*Psidium Guajava Linn*) with a specific extraction solvent is subjected to fractionation by high performance liquid chromatography under specific conditions.

Guava, also called banjiro or banzakuro in Japan, is a small evergreen tree belonging to the genus *Psidium* of the family Myrtaceae that is native to tropical regions. Guava grows naturally, for example, along Caribbean coasts, in Central America, in north of South America, and in Southeast Asia and is cultivated in warm places, such as Okinawa, in Japan.

As raw material to be used for the extraction of a guava extract, any organ of a guava or constituents of any organ of a guava can be used. The raw material for extraction may be a single organ of a guava or its constituents or may be a mixture of two or more organs of a guava or their constituents. To obtain a guava extract that is excellent in an anti-avian influenza virus effect, the raw material for extraction preferably contains at least a leaf or a stem of a guava.

The raw material for extraction is subjected to an extraction operation in the state when it is harvested, in the state that it is crushed, pulverized, or ground after the harvest, in the state that it is dried after the harvest, in the state that it is crushed, pulverized, or ground after the harvest and drying, or in the state that it is crushed, pulverize, or ground after the harvest and then is dried. To perform extraction efficiently, the raw material for extraction is preferably crushed. To obtain a guava extract that is excellent in an anti-avian influenza virus effect, the raw material for extraction is preferably a raw leaf.

The extraction solvent used for extracting a guava extract from the raw material for extraction consists primarily of at least one of water and a hydrophilic organic solvent. That is, at least one of water and a hydrophilic organic solvent exists in the highest proportion (% by volume) in the extraction solvent. The content of water or a hydrophilic organic solvent in the extraction solvent is preferably 50% by volume or higher, more preferably 70% by volume or higher. When the extraction solvent contains both water and a hydrophilic organic solvent, the total content of water and the hydrophilic organic solvent is preferably 50% by volume or higher, more preferably 70% by volume or higher.

Examples of the hydrophilic organic solvent contained in the extraction solvent include lower alcohols such as methanol and ethanol, acetone, and ethyl acetate. The extraction solvent may contain one hydrophilic organic solvent solely or two or more hydrophilic organic solvents. The extraction solvent may contain a small amount of solvents other than water and a hydrophilic organic solvent. An organic salt, an inorganic salt, a buffer, or an emulsifier, for example, may be dissolved in the extraction solvent.

Extraction of a guava extract is performed by immersing a raw material for extraction in the extraction solvent for a predetermined time. At this time, if necessary, the extraction solvent may be stirred, heated, or pressurized. In general, when the extraction temperature is elevated, the time required for extraction is reduced. For example, while extraction at room temperature under a pressure of 1 to 2 atmosphere takes as long as 10 days, extraction takes only 0.05 to 2 hours or 0.1 to 0.3 hours at a temperature of 50 to 130° C. The extraction conditions can be suitably changed depending on the conditions of the raw material for extraction or the type of the extraction solvent.

The guava extract extracted from the raw material for extraction is subjected to solid-liquid separation to separate and remove residues of the raw material for extraction. Solid-liquid separation is performed, for example, by a known method such as filtration or centrifugation.

After solids are removed by solid-liquid separation, the guava extract is subsequently subjected to fractionation by high performance liquid chromatography under specific conditions. An ODS column having an inside diameter of 20 mm and a length of 250 mm is used in this fractionation by high performance liquid chromatography. The ODS column is filled with a solid phase, i.e., with a chemically bonded porous spherical silica gel of which surface is modified with an octadecylsilyl group having 18 carbon atoms. The ODS column may be, for example, SH-343-5 (the silica gel particle size is 5 μm, and the slit diameter is 12 nm) manufactured by YMC Co., Ltd. A mixed solution of water and methanol is used as a mobile phase. After applying a guava extract to the ODS column, the methanol concentration of the mixed solution is changed stepwise as each predetermined time elapses along a gradient curve shown in the graph of FIG. 1(a). Specifically, the methanol concentration of the mixed solution is 20% during a period until 15 minutes (0 to 15 minutes) after applying the guava extract to the ODS column, 40% during a subsequent period of 15 to 30 minutes, and 60% during a subsequent period 30 to 45 minutes. The flow rate of the mobile phase is set as 10 mL/min. The column temperature is preferably room temperature (25° C.).

The anti-avian influenza virus agent of this embodiment contains, as an active ingredient, a component eluted from the ODS column in a first period until 20 minutes (0 to 20 minutes) after applying the guava extract to the column or a component eluted from the ODS column in a subsequent second period of 20 to 35 minutes. The anti-avian influenza virus agent may be an eluate itself eluted from the column in the first period or the second period, or a product obtained by powdering the eluate by a known drying treatment such as freeze-drying. The product obtained by powdering the eluate in the first period is brownish-red and slightly sticky, while the product obtained by powdering the eluate in the second period is brownish-red and powdery.

The anti-avian influenza virus agent can be applied to a product used for the purpose of exerting an anti-avian influenza virus effect. Examples of such an anti-avian influenza virus agent-containing product include medical agents (including medicines), cleaning agents, cosmetics, medical apparatuses, hygiene materials, hygiene products, foods, and drinks. Examples of the medical agents include drugs. Examples of the cleaning agents include laundry softeners, laundry bleaches, soaps, bath agents, detergents, shampoos, and toothpastes. Examples of the cosmetics include facial soaps, hand soaps, hand creams, perfumes, lotions, milky lotions, beauty essences, beauty creams, lipsticks, lip creams, and face powders. Examples of the medical apparatuses include masks, bandages, gauzes, gloves, sticking plasters, swabs, diagnostic instruments and apparatuses, surgery instruments and apparatuses, therapeutic instruments and apparatuses, hospital instruments and apparatuses, dental instruments and apparatuses, auxiliary medical instruments, and orthotics. Examples of the hygiene materials include gauzes, absorbent cotton, non-woven fabrics, and cotton-tipped sticks. Examples of the hygiene products include humidifiers, air-conditioners, and air cleaners. Examples of the foods and drinks include healthy drinks and healthy foods. Examples of the medical agents and the cosmetics also include quasi-drugs such as mouthwashes, throat lozenges, throat sprays, medical soaps, and antiseptics.

Drugs and quasi-drugs that contain an anti-avian influenza virus agent can be administered by any method, such as oral administration, intravascular administration, or percutaneous administration. Dosage forms of the drugs and quasi-drugs are not particularly limited, and the drugs and quasi-drugs may be, for example, powder, dust formulation, granule, tablet, capsule, pill, suppository, solution, injection, or liniment. The drugs and quasi-drugs may contain an additive such as an excipient, a base material, an emulsifier, a solvent, and a stabilizer so long as the additives do not hinder achievement of the objective of the present invention.

Foods and drinks that contain an anti-avian influenza virus agent are produced by adding the anti-avian influenza virus agent to arbitrary food materials or drink materials. The foods and drinks are processed in the forms of, for example, powder, tablet, granule, liquid (drinkable preparation and the like), capsule, syrup, and candy and can be used as healthy food products and dietary supplement foods. Specific examples of the foods and drinks include sports drinks, tea drinks extracted from tea leaves, herbs, and the like, dairy products such as cow's milk and yogurt, foods containing gelatinizing agents such as pectin and carrageenan, candies such as hard candies, soft candies, and gummy sweets, chewing gums, and foods and drinks containing a saccharide such as glucose, sucrose, fructose, lactose, and dextrin, a flavor, a sweetener such as stevia, aspartame, and a sugar alcohol, an oil and fat such as a plant oil and fat and an animal oil and fat. The foods and drinks may contain an additive such as a base material, an excipient, an additive, a submaterial, and an extender so long as the additives do not hinder achievement of the objective of the present invention.

Avian influenza virus is classified into subtypes such as H5N3, H5N1, H5N7, H5N2, and H7N3 depending on the types of hemagglutinin and neuraminidase, and the anti-avian influenza virus agent of this embodiment can be used against any type of avian influenza virus.

According to this embodiment, the following advantages can be obtained.

The anti-avian influenza virus agent of this embodiment has an excellent anti-avian influenza virus effect. This anti-avian influenza virus agent can therefore be used for the treatment of farm animals, including domestic poultry, and humans infected with avian influenza virus and for prevention of avian influenza virus infection in healthy farm animals, including domestic poultry, and humans. That is, the anti-avian influenza virus agent is useful as an agent for the prevention or treatment of avian influenza.

Since the anti-avian influenza virus agent of this embodiment is an extract derived from a guava, which is a natural plant, the anti-avian influenza virus agent of this embodiment has high level of safety.

The above-mentioned embodiment may be modified as described below.

The anti-avian influenza virus agent may be a product obtained by treating an eluate eluted from the ODS column in a first period (until 20 minutes after applying a guava extract to the column) or a second period (a subsequent period of 20 to 35 minutes) with polyvinylpolypyrrolidone (PVPP). In this case, components adsorbed to polyvinylpolypyrrolidone can be removed.

Hereafter, the present invention will be more specifically described with reference to examples.

<Preparation of Anti-Avian Influenza Virus Agent>

1 kg of raw guava leaves were cut into pieces having a size of approx. 1 square centimeter and immersed in 10 L of aqueous ethanol solution containing ethanol and water in a ratio of 3:7 at room temperature for 10 days. Then, a filtrate obtained by filtering this solution was concentrated and dried to give 65.1 g of powdery guava extract. Out of this guava extract, 6.5 g was dissolved in 50 mL of aqueous methanol solution containing methanol and water in a ratio of 2:1. The obtained solution was centrifuged at 3000 rpm for 15 minutes. Then, the supernatant was filtered through a cellulose acetate filter (DISMIC-25CS080AN) having a pore size of 0.80 µm manufactured by Advantec MFS Inc., and the filtrate was collected as a sample for separation. Then, the sample for separation was subjected to fractionation by high performance liquid chromatography under the following conditions:

(Conditions of Fractionation by High Performance Liquid Chromatography)

Column: SH-343-5 (the inside diameter and length of the column were 20 mm and 250 mm, respectively, the silica gel particle size 5 µm, and the slit diameter 12 nm) manufactured by YMC Co., Ltd.

Mobile phase: A water-methanol mixture having a methanol concentration of 20% during a period until 15 minutes (0 to 15 minutes) after applying the sample for separation to the column, a water-methanol mixture having a methanol concentration of 40% during a subsequent period of 15 to 30 minutes, a water-methanol mixture having a methanol concentration of 60% during a subsequent period of 30 to 45 minutes, and 100% methanol during a subsequent period of 45 to 50 minutes (see FIG. 1(a))

Flow rate of mobile phase: 10 mL/min
Column temperature: room temperature (25° C.)
Detection wavelength: 255 nm The HPLC chart obtained at this time is shown in FIG. 1(b). Six fractions were obtained at different times after applying the sample for separation to the column, i.e., different elution times. More specifically, the eluates eluted from the column in the period until 20 minutes (0 to 20 minutes) after applying the sample for separation to the column, in the subsequent period of 20 to 35 minutes, in the subsequent period of 35 to 39 minutes, in the subsequent period of 39 to 41 minutes, in the subsequent period of 41 to 43 minutes, and in the subsequent period of 43 to 50 minutes were collected separately, and the six obtained fractions were concentrated and dried to give six powders A to F shown in Table 1.

TABLE 1

| Powders | Elution time (min) | Yield (mg) |
| --- | --- | --- |
| A | 0-20 | 2796 |
| B | 20-35 | 780 |
| C | 35-39 | 11 |
| D | 39-41 | 135 |
| E | 41-43 | 157 |
| F | 43-50 | 33 |

Powders A to F were dissolved in an aqueous ethanol solution (10 to 90%) at a concentration of 0.5% w/v to prepare samples A to F. Likewise, the powdery guava extract obtained above was dissolved in an aqueous ethanol solution (10 to 90%) at a concentration of 0.5% w/v to prepare a sample Mx. Samples A to F and sample Mx were subjected to analysis by high performance liquid chromatography under the following conditions:

(Conditions of Analysis by High Performance Liquid Chromatography)

Column: Cadenza CD-C18 (CD006: the inside diameter was 4.6 mm, the length 250 mm, and the particle size 3 µm) manufactured by Imtakt Corporation Mobile phase: a water-acetic acid-methanol mixture having a methanol concentration of 10% and an acetic acid concentration of 5% until 10 minutes (0 to 10 minutes) after applying the sample to the column, a water-acetic acid-methanol mixture having a linearly gradually increased methanol concentration of 10% to 35% during a subsequent period of 10 to 20 minutes, a water-acetic acid-methanol mixture having a methanol concentration of 35% and an acetic acid concentration of 5% during a subsequent period of 20 to 40 minutes, a water-acetic acid-methanol mixture having a linearly gradually increased methanol concentration of 35% to 100% during a subsequent period of 40 to 50 minutes, and 100% methanol during a subsequent period of 50 to 60 minutes (see FIG. 2(a))

Figure 2B:
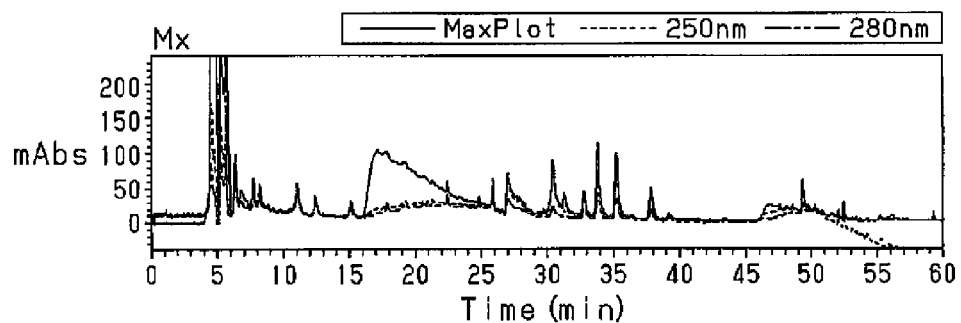
FIG. 2(b) is an HPLC chart obtained from high performance liquid chromatography analysis of sample Mx.
Figure 2C:
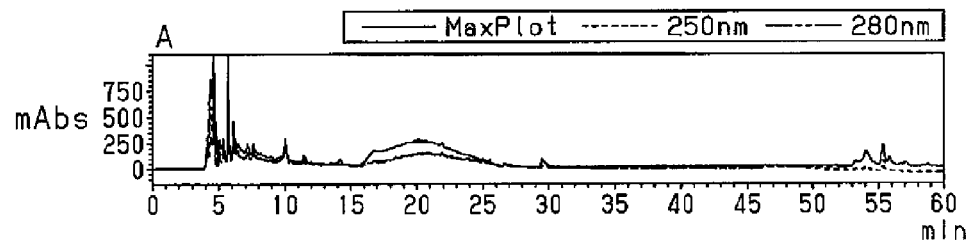
FIG. 2(c) is an HPLC chart obtained from high performance liquid chromatography analysis of sample A.
Figure 2D:
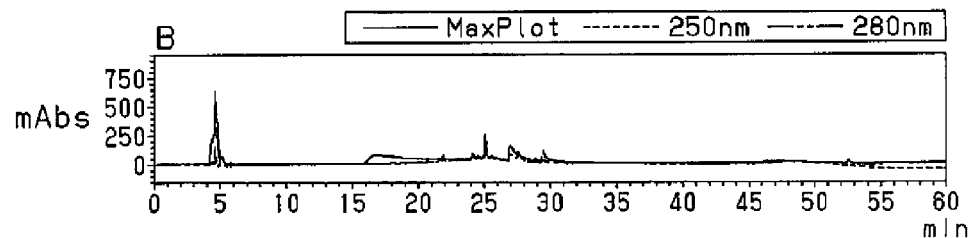
FIG. 2(d) is an HPLC chart obtained from high performance liquid chromatography analysis of sample B.
Figure 3A:
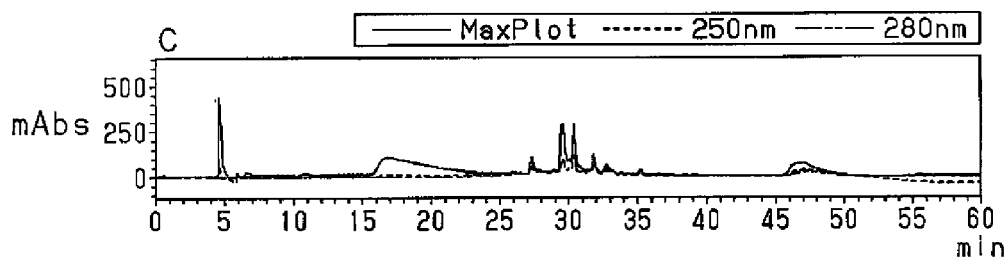
FIG. 3(a) is an HPLC chart obtained from high performance liquid chromatography analysis of sample C.
Figure 3B:
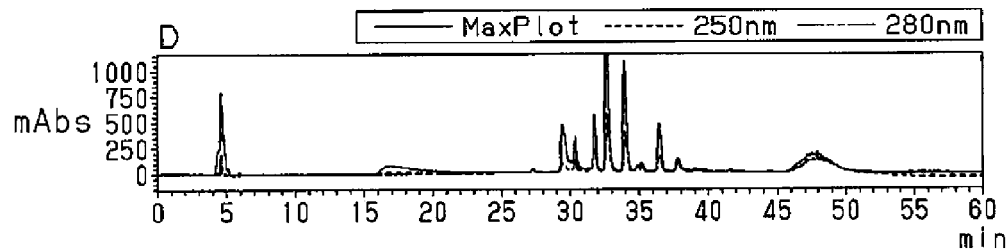
FIG. 3(b) is an HPLC chart obtained from high performance liquid chromatography analysis of sample D.
Figure 3C:
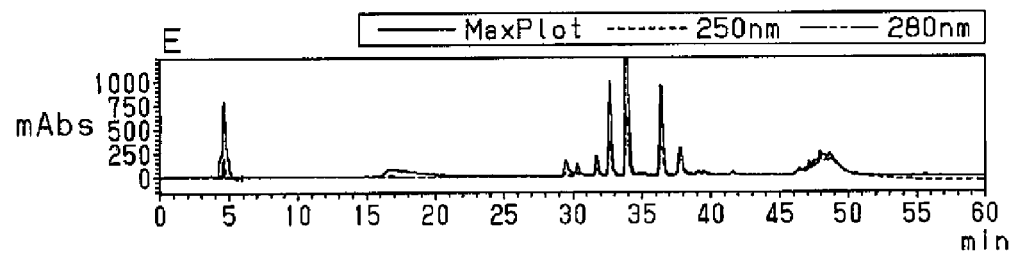
FIG. 3(c) is an HPLC chart obtained from high performance liquid chromatography analysis of sample E.
Figure 3D:
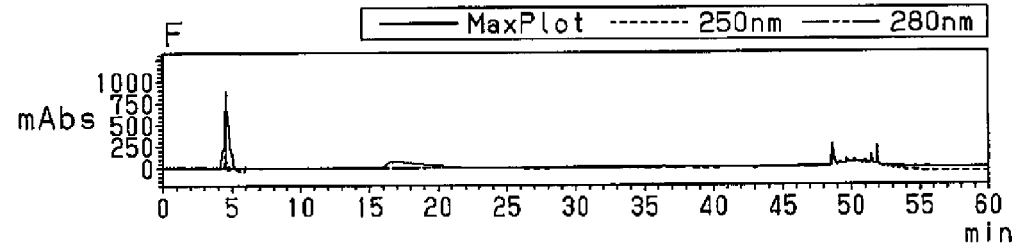
FIG. 3(d) is an HPLC chart obtained from high performance liquid chromatography analysis of sample F.

Flow rate of mobile phase: 0.6 mL/min
Column temperature: 40° C.
Detection wavelengths: MaxPlot (190 to 800 nm), 250 nm, 280 nm The HPLC charts obtained in this analysis are shown in FIGS. 2(b) to 2(d) and FIGS. 3(a) to 3(d). More specifically, FIG. 2(b) shows the HPLC chart of sample Mx, FIG. 2(c) shows the HPLC chart of sample A, and FIG. 2(d) shows the HPLC chart of sample B. FIG. 3(a) shows the HPLC chart of sample C, FIG. 3(b) shows the HPLC chart of sample D, FIG. 3(c) shows the HPLC chart of sample E, and FIG. 3(d) shows the HPLC chart of sample F.

<Test of Anti-Avian Influenza Virus Effect>

Anti-avian influenza virus effects of the above-mentioned samples A to F and sample Mx were evaluated by the procedure described below.

First, MDCK cells (canine kidney epithelial cells) were cultured on a 96-well culture plate using MEM medium containing 7% FBS in a $CO_2$ incubator set at 37° C. for 2 days to form a monolayer of MDCK cells. A stock solution of avian influenza virus (H5N3: A/Duck/313/4/78 virus) was diluted with serum-free medium (SF-MEM) to prepare 0.7 HAU of a viral solution. The viral solution was mixed with an equal volume of each of diluted solutions obtained by diluting each of samples A to F and sample Mx 25-fold, 100-fold, 400-fold, 1600-fold, 6400-fold, and 25600-fold (a concentration double that at inoculation) with serum-free medium (SF-MEM), and the mixtures were left at 4° C. for 1 hour to prepare virus sample mixtures. 100 µL of each virus sample mixture was inoculated into MDCK cells grown in a monolayer on the 96-well culture plate, and infection treatment was performed in a $CO_2$ incubator at 34° C. The virus sample mixtures were removed after 1 hour, and the cultured cells on the culture plate were washed with serum-free medium (SF-MEM).

Then, each of samples A to F and sample Mx was diluted 50-fold, 200-fold, 800-fold, 3200-fold, 12800-fold, and 51200-fold with serum-free medium (SF-MEM) containing 2.5 L of acetyl trypsin. 100 µL of each of the obtained diluted solutions was added to a cell of MDCK cells inoculated with the virus sample mixture containing guava extract-derived components at the same concentrations as above, and the culture plate was placed in a $CO_2$ incubator set at 34° C. At 18 hours, 50 µL of methanol was added to each cell, and the culture plate was left at room temperature for 1 minute to immobilize MDCK cells. Then, the cells were washed with serum-free medium (SF-MEM). Then, an anti-nucleoprotein-monoclonal antibody (4E6) was added to each cell, the culture plate was left at room temperature for 45 minutes, and then the cells were washed with serum-free medium (SF-MEM). Then, anti-mouse IgG-labeled β-galactosidase (0.1% Block Ace) was added to each cell, and the culture plate was left at room temperature for 45 minutes.

Figure 4A:
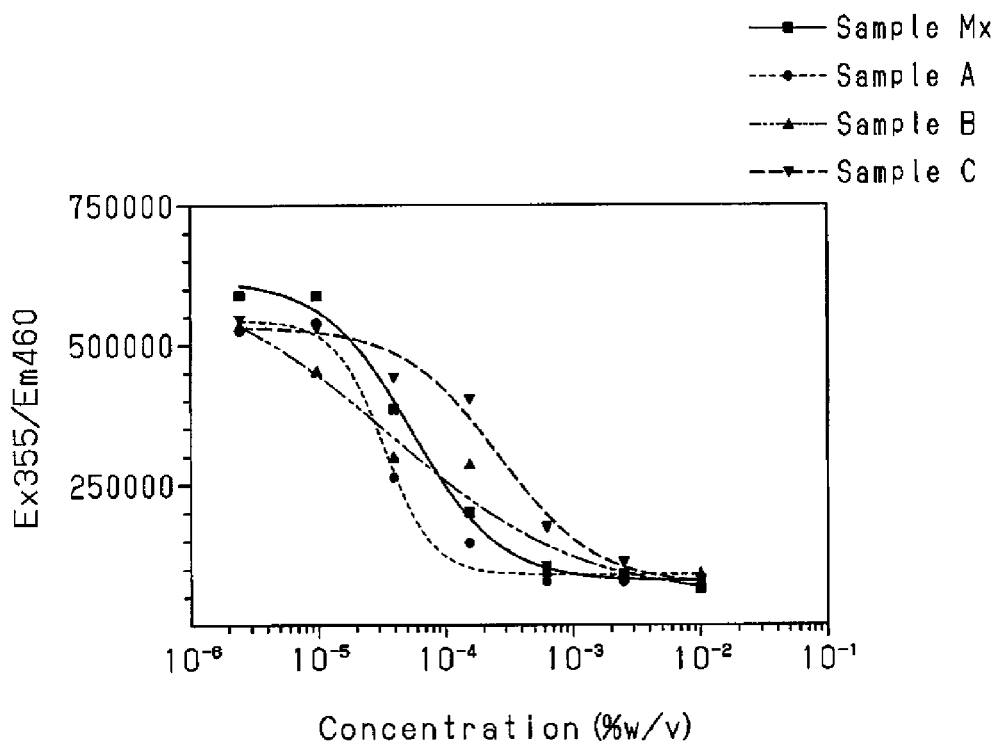
FIGS. 4(a) and 4(b) are graphs showing the relationships between the concentrations of components of a guava extract in virus sample mixtures and the measured fluorescence intensities.
Figure 4B:
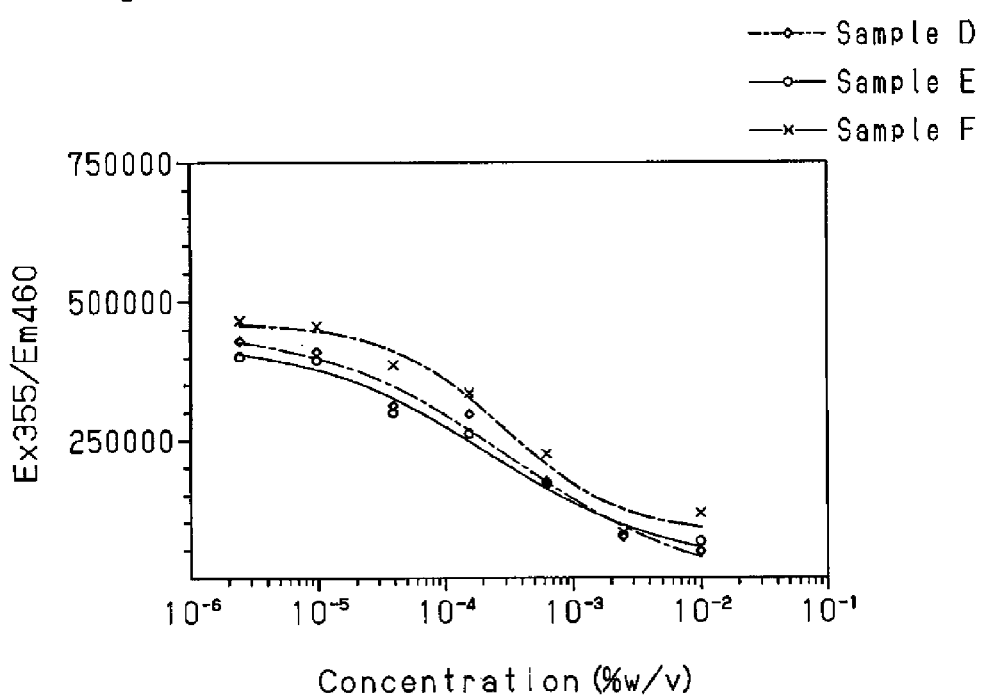

Then, 40 µM 4-methylumbelliferone (MU)-Gal (containing 50 µM $MgCl_2$) was added to each cell, and the culture plate was maintained at 37° C. for 45 minutes. At this time, anti-mouse IgG-labeled β-galactosidase produces fluorescent 4-methylumbelliferone (MU) using MU-Gal as a substrate. Then, 100 mM sodium carbonate buffer (pH 10.6) was added to each cell to terminate the reaction, and the amount of virus that infected cells was indirectly determined by measuring the amount of MU produced. The amount of MU produced was measured at an excitation wavelength of 355 nm and a fluorescence wavelength (detection wavelength) of 460 nm using a fluorescence detector. Graphs showing the relationships between the concentrations of the guava extract-derived components in the virus sample mixtures and the fluorescence intensities obtained based on the results of this measurement are shown in FIGS. 4(a) and 4(b). The concentrations at which 50% of the effect is observed ($EC_{50}$) were calculated for each sample. The results are shown in Table 2.

TABLE 2

| Samples | $EC_{50}$ (% w/v) |
|---|---|
| A | $3.28 \times 10^{-5}$ |
| B | $3.52 \times 10^{-5}$ |
| C | $26.22 \times 10^{-5}$ |
| D | $33.52 \times 10^{-5}$ |
| E | $22.31 \times 10^{-5}$ |
| F | $29.64 \times 10^{-5}$ |
| Mx | $5.37 \times 10^{-5}$ |

As shown in Table 2, it was confirmed that sample Mx, which contained a guava extract, had a high anti-influenza virus effect. Further, as samples A and B exhibited a particularly high anti-influenza virus effect among samples A to F, it was confirmed that powders A and B played a key role in exhibition of the anti-influenza virus effect by a guava extract.

<Test of Treatment with Polyvinylpolypyrrolidone>

Changes in the anti-influenza virus effect after treatment of samples A and B with polyvinylpolypyrrolidone (PVPP) were examined. PVPP has an action of adsorbing polymerized polyphenols such as tannin, and most of polyphenols contained in samples A and B are removed by treatment with PVPP.

First, 5.0 g/L of PVPP was added to 1 mL of each of samples A and B, and the mixtures were stirred. The mixtures were centrifuged at 10000 rpm for 5 minutes, and the supernatant was filtered through a cellulose acetate filter (DISMIC-25CS080AN) having a pore size of 0.80 µm manufactured by Advantec MFS Inc. to collect the filtrate. The obtained PVPP-treated samples A and B as described above and PVPP-untreated samples A and B were compared for the anti-influenza virus effect by the following method.

First, MDCK cells (canine kidney epithelial cells) were cultured on a 24-well culture plate using 7% FBS-containing MEM in a $CO_2$ incubator set at 37° C. for 2 days to form a monolayer of MDCK cells. A stock solution of avian influenza virus (H5N3: A/Duck/313/4/78 virus) was diluted with serum-free medium (SF-MEM) to prepare 0.7 HAU of a viral solution. Then, PVPP-treated samples A and B and PVPP-untreated A and B were diluted 200-fold with serum-free medium (SF-MEM), and each of the obtained dilution samples was further diluted 25-fold, 100-fold, 400-fold, 1600-fold, 6400-fold, and 25600-fold (a concentration double that at inoculation) with serum-free medium (SF-MEM) and mixed with an equal volume of the viral solution. The obtained virus sample mixtures were left on ice for 1 hour. Then, 200 µL of each virus sample mixture was inoculated into MDCK cells grown in a monolayer on the 24-well culture plate, and infection treatment was performed in a $CO_2$ incubator set at 34° C.

At 1 hour, the virus sample mixtures were removed, and the cultured cells on the culture plate were washed with serum-free medium (SF-MEM). Then, 0.75% agarose-containing MEM medium was overlaid on the cells, and the cells were cultured in a $CO_2$ incubator set at 34° C. for 3 days. Then, an ethanol-acetic acid solution containing ethanol and acetic acid in a ratio of 5:1 was added to each cell, the culture plate was allowed to stand overnight, infection was terminated, and MDCK cells were immobilized. Then, the overlaid medium removed, the cells were washed with pure water and 0.1% Triton PBS solution and then reacted with a primary antibody and a secondary antibody. Then, the cells were treated with a staining solution (DEPDA, 4CN citrate buffer, $H_2O_2$), and the numbers of plaques colored in blue were counted to evaluate the suppression rate of avian influenza virus infection. The results are shown in Table 3.

TABLE 3

| Samples | Viral suppression rate (%) |
|---|---|
| PVPP-untreated sample A | 92.1 |
| PVPP-treated sample A | 95.1 |
| PVPP-untreated sample B | 99.7 |
| PVPP-treated sample B | 100 |

As shown in Table 3, the viral suppression rates of samples A and B were not decreased by treatment with PVPP. These results suggest that components contained in samples A and B that showed the anti-avian influenza virus effect may not be polymerized polyphenols, such as tannin. Therefore, treatment with PVPP is effective to remove components that are not components exhibiting the anti-avian influenza virus effect and thereby increase the content of the components exhibiting the anti-avian influenza virus effect.

The invention claimed is:

1. An anti-avian influenza virus agent comprising, as an active ingredient, a guava component, wherein the guava component is obtained by a process comprising:
   extracting guava leaves with an extraction solvent consisting primarily of at least one of water and a hydrophilic organic solvent to form an extract;
   subjecting the extract to high performance liquid chromatography fractionation by first applying the extract to an ODS column having an inside diameter of 20 mm and a length of 250 mm, and adding a water-methanol mixture having a methanol concentration of 20% as a mobile phase to the ODS column during an initial period of 15 minutes after applying the guava extract to the ODS column;
   adding a water-methanol mixture having a methanol concentration of 40% as a mobile phase to the ODS column during a subsequent period of 15 to 30 minutes;
   adding a water-methanol mixture having a methanol concentration of 60% as a mobile phase to the ODS column during a subsequent period of 30 to 45 minutes;
   eluting the guava component from the ODS column over a period of 0 to 20 minutes after applying the guava extract to the column, and/or over a period of 20 to 35 minutes after applying the guava extract to the column; and
   contacting the guava component with polyvinylpolypyrrolidone to adsorb and remove polyphenols therefrom.

2. The anti-avian influenza virus agent according to claim 1, wherein guava component is eluted from the ODS column over a period of 0 to 20 minutes after applying the guava extract to the column.

3. The anti-avian influenza virus agent according to claim 2, which is used as an agent for the treatment or reduction of the risk of developing avian influenza.

4. The anti-avian influenza virus agent according to claim 3, wherein the avian influenza is of H5N3 or H5N1 strain.

5. An anti-avian influenza virus agent-containing product comprising an effective amount of the anti-avian influenza virus agent according to claim 2.

6. The anti-avian influenza virus agent according to claim 1 wherein the guava component is eluted from the ODS column over a period of 20 to 35 minutes after applying the guava extract to the column.

7. The anti-avian influenza virus agent according to claim 6, which is used as an agent for the treatment or reduction of the risk of developing avian influenza.

8. An anti-avian influenza virus agent-containing product comprising an effective amount of the anti-avian influenza virus agent according to claim 6.

9. A method of treating or reducing the risk of developing avian influenza comprising administering to a human or a farm animal the anti-avian influenza virus agent according to claim 2.

10. The method according to claim 9, wherein the avian influenza is of H5N3 or H5N1 strain.

11. A method of treating or reducing the risk of developing avian influenza comprising administering to a human or a farm animal the anti-avian influenza virus agent according to claim 6.

12. A method for producing an anti-avian influenza virus agent containing, as an active ingredient, a guava component, comprising:
   extracting guava leaves with an extraction solvent consisting primarily of at least one of water and a hydrophilic organic solvent to form an extract;
   subjecting the extract to high performance liquid chromatography fractionation by first applying the extract to an ODS column having an inside diameter of 20 mm and a length of 250 mm, and adding a water-methanol mixture having a methanol concentration of 20% as a mobile phase to the ODS column during an initial period of 15 minutes after applying the guava extract to the ODS column;
   adding a water-methanol mixture having a methanol concentration of 40% as a mobile phase to the ODS column during a subsequent period of 15 to 30 minutes;
   adding a water-methanol mixture having a methanol concentration of 60% as a mobile phase to the ODS column during a subsequent period of 30 to 45 minutes;
   eluting the guava component from the ODS column over a period of 0 to 20 minutes after applying the guava extract to the column, and/or over a period of 20 to 35 minutes after applying the guava extract to the column; and
   contacting the guava component with polyvinylpolypyrrolidone to adsorb and remove polyphenols therefrom.

* * * * *